(12) United States Patent  (10) Patent No.: US 8,979,850 B2
Johnstone  (45) Date of Patent: Mar. 17, 2015

(54) SURGICAL GUIDE DEVICE

(75) Inventor: Alan Johnstone, Aberdeen (GB)

(73) Assignee: Clear Surgical Limited, Glasgow (GB)

( * ) Notice: Subject to any disclaimer, the term of this patent is extended or adjusted under 35 U.S.C. 154(b) by 163 days.

(21) Appl. No.: 13/701,246

(22) PCT Filed: Jun. 3, 2011

(86) PCT No.: PCT/GB2011/051051
§ 371 (c)(1),
(2), (4) Date: Feb. 21, 2013

(87) PCT Pub. No.: WO2011/151654
PCT Pub. Date: Dec. 8, 2011

(65) Prior Publication Data
US 2013/0144351 A1  Jun. 6, 2013

(30) Foreign Application Priority Data
Jun. 3, 2010 (GB) .................................. 1009319.3

(51) Int. Cl.
A61F 2/46 (2006.01)
A61F 5/00 (2006.01)
A61B 17/88 (2006.01)
A61B 17/17 (2006.01)
A61B 17/84 (2006.01)
A61B 17/90 (2006.01)

(52) U.S. Cl.
CPC ............. *A61B 17/8866* (2013.01); *A61B 17/17* (2013.01); *A61B 17/848* (2013.01); *A61B 17/8897* (2013.01); *A61B 2017/90* (2013.01)
USPC .......................................... 606/86 R; 606/87

(58) Field of Classification Search
CPC ............................ A61B 17/17; A61B 2017/90
USPC ....... 606/205–209, 324, 96–98, 86 R, 87–89, 606/102, 104–105
See application file for complete search history.

(56) References Cited

U.S. PATENT DOCUMENTS

| 4,883,048 A | 11/1989 | Purnell et al. |
| 5,312,412 A | 5/1994 | Whipple |
| 5,514,144 A | 5/1996 | Bolton |
| 5,725,532 A | 3/1998 | Shoemaker |

(Continued)

FOREIGN PATENT DOCUMENTS

| CN | 2451058 | 10/2001 |
| CN | 201073337 | 6/2008 |

(Continued)

OTHER PUBLICATIONS

Innomed, "*Chang Pin Clamp*", www.innomed.net, 2007.

(Continued)

*Primary Examiner* — Sameh Boles
(74) *Attorney, Agent, or Firm* — Diederiks & Whitelaw, PLC

(57) ABSTRACT

A surgical guide device comprises first and second limbs pivotally connected together, with a respective guide sleeve pivotally attached to each limb. Each guide sleeve has a bore through the sleeve that can guide a drill bit or bone fixing for insertion into a fragmented bone portion. The device has an orientation mechanism adapted to change the orientation of the guide sleeves relative to the limbs as the limbs move relative to one another, so as to maintain the orientation of the guide sleeves relative to one another during pivotal movement of the limbs.

36 Claims, 7 Drawing Sheets

(56) References Cited

U.S. PATENT DOCUMENTS

| | | |
|---|---|---|
| 2004/0162561 A1 | 8/2004 | Marchyn et al. |
| 2008/0177394 A1 | 7/2008 | Chauhan |
| 2009/0254130 A1* | 10/2009 | Wotton, III .................. 606/324 |
| 2009/0306675 A1 | 12/2009 | Wong et al. |

FOREIGN PATENT DOCUMENTS

| | | |
|---|---|---|
| DE | 102007008918 | 8/2008 |
| EP | 2067443 | 6/2009 |
| FR | 2560764 | 9/1985 |
| WO | WO 01/82805 | 11/2001 |
| WO | WO 2005/016131 | 2/2005 |
| WO | WO 03/045258 | 6/2006 |
| WO | WO 2007/137327 | 12/2007 |

OTHER PUBLICATIONS

Innomed, "*Redler Percutaneous Pin Clamp*", www.innomed.net, 2002.

\* cited by examiner

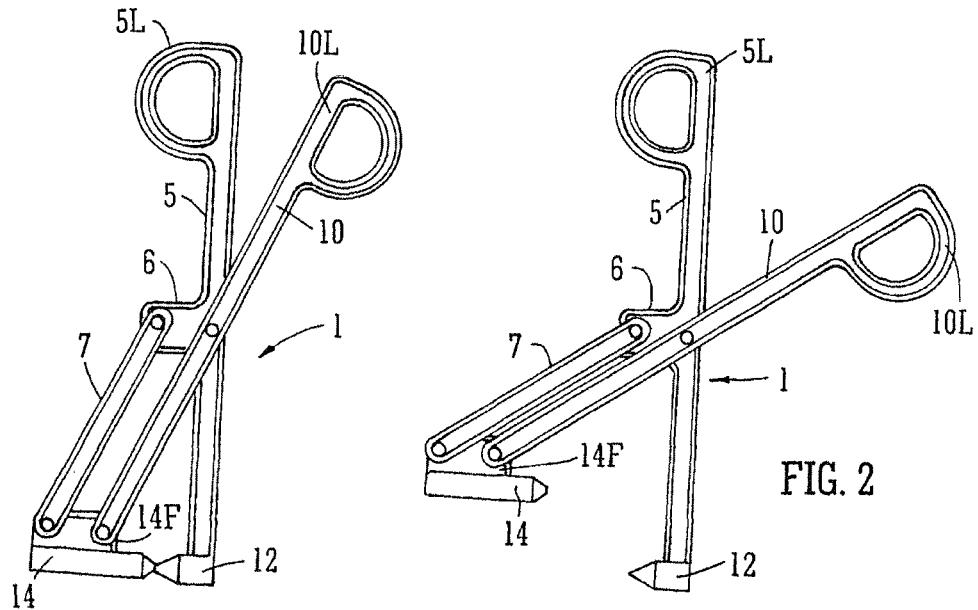
FIG. 1
FIG. 2
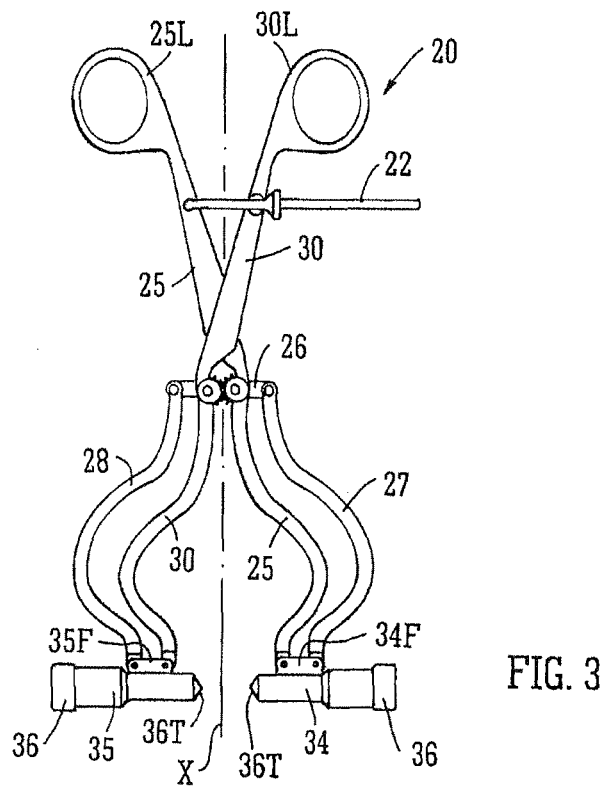
FIG. 3

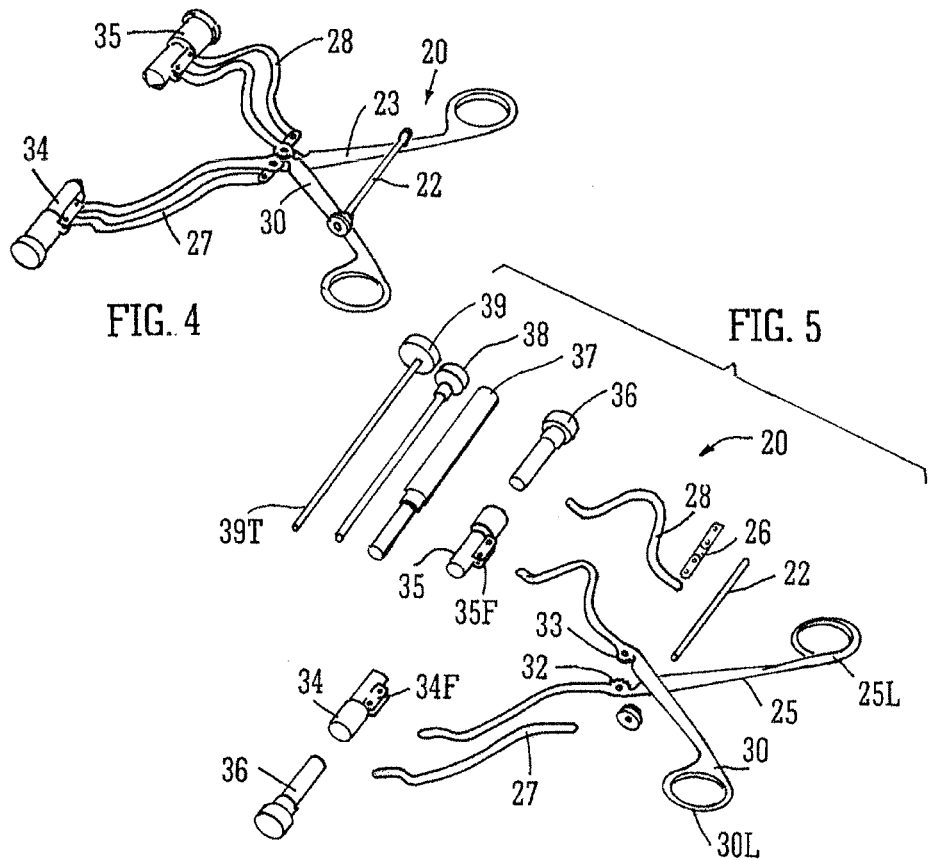
FIG. 4
FIG. 5
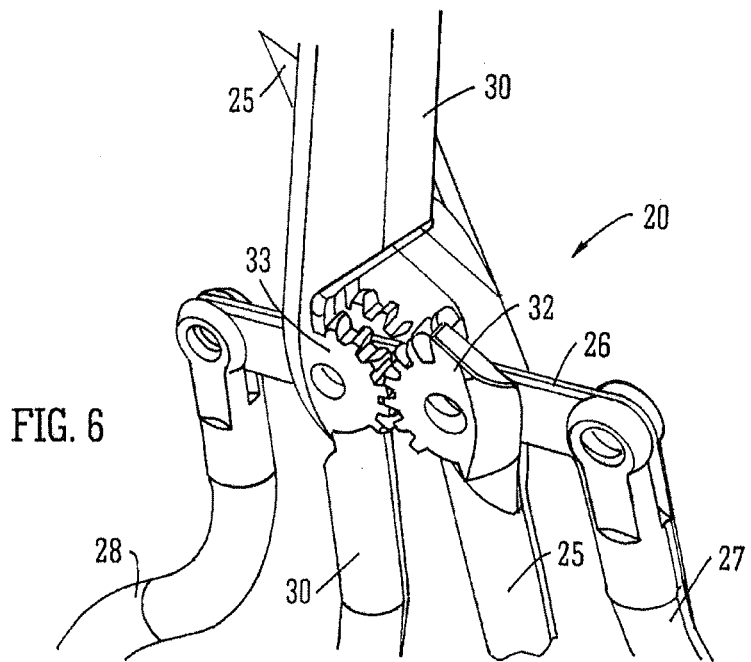
FIG. 6

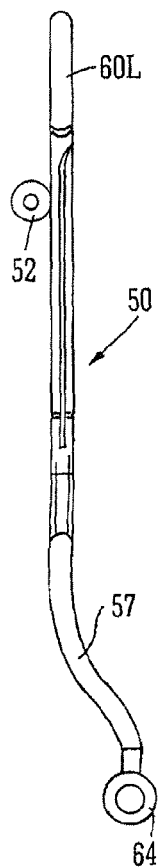
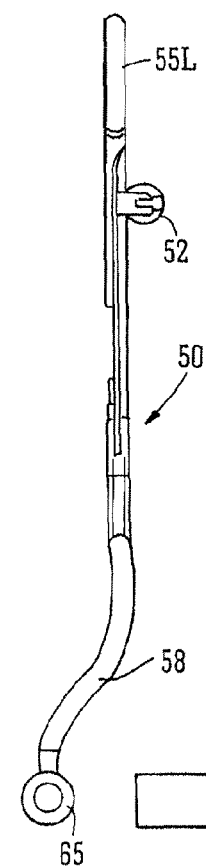
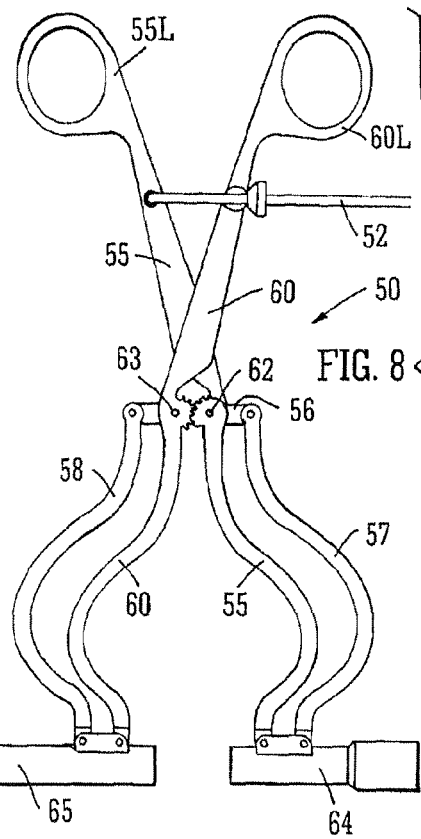

SURGICAL GUIDE DEVICE

CROSS-REFERENCE TO RELATED APPLICATIONS

This application represents a National Stage application of PCT/GB2011/051051 entitled "Surgical Guide Device" filed Jun. 3, 2011, pending.

BACKGROUND OF THE INVENTION

The present invention relates to a surgical guide device, particularly but not exclusively to a reduction clamp device for supporting bone fragments in a fixed position during surgical intervention, for example while a pin or other bone fixing is inserted through the bone fragments. The invention also relates, in some aspects, to a method of guiding the insertion of a fixing device into a portion of the body such as a bone fracture.

Often during the reduction of bone fractures (the clamping and fixing of two or more bone fragments together) the best site for clamping the two bone fragments together is often also the best site for inserting a fixation system e.g. drilling and inserting a pin or screw. However, since the ideal fixation site is typically blocked by the reduction device, the surgeon often has to insert the fixation device in a less than ideal position next to the reduction device. The surgeon may also be forced to insert the fixation system at an obtuse angle, in order to get as close to the ideal fixation point as possible. This may ultimately lead to the possibility of non-ideal healing and strength of the repaired bone.

Existing devices to support bone portions for pinning or other intervention are known, for example from U.S. Pat. No. 5,725,532, which essentially comprises a drill guide on the end of one limb of a scissor arrangement. Bone fragments are held together by the device while a drill is passed through the drill guide to drill a hole for a screw or other device to fix the bone portions together.

A problem with such scissor-type devices is that there is only a small range of angles between the two limbs of the device for which the longitudinal axis of the drill guide points directly at the opposite tip of the other limb of the scissor. Accordingly such devices can only be used for a particular bone diameter and multiple devices will be required to accommodate different bones sizes. For example, if such a device were to be used to clamp a larger bone diameter that that for which it is designed, the longitudinal axis of the drill guide would point beyond the tip of the other limb of the scissor, which would lead to non-ideal conditions for reducing, drilling and pinning the bone due to instability of the device clamped on the bone fragments. There remains a need for a surgical guide device that can accurately guide the insertion of a fixing device into a number of different bones of various diameters. It is an aim of the present invention to provide improved devices and methods for reducing bone fractures.

SUMMARY OF THE INVENTION

According to a first aspect of the present invention there is provided a surgical guide device comprising first and second limbs pivotally connected together, at least one guide sleeve attached to one limb, the guide sleeve having a bore through the sleeve, wherein the guide sleeve is pivotally attached to the limb, and wherein the apparatus has an orientation mechanism adapted to change the orientation of the guide sleeve relative to the limb as the limbs move relative to one another.

It is advantageous when reducing a fracture, that the bore through the guide sleeve always points directly towards the opposite point on the other limb of the device, regardless of what sized bone the surgeon is dealing with. This will allow for the most stable clamping conditions and accurate positioning of the bone fixing (e.g. screw, wire nail). The device can be used on a wide range of bone diameters whilst always having the guide sleeve in alignment with the same point on the opposite limb, so that a surgeon will always know with accuracy where a drill bit or fixing guided by the sleeve will enter and exit the bone. Because the surgeon can identify or predict the path of a drill bit or fixing through the guide sleeve(s), there is a reduced risk of drilling through sensitive or critical tissues, and it is ensured that the fixing is anchored in solid tissues that are more capable of withstanding forces tending to dislodge the fixing after insertion. Furthermore the surgeon can better judge the correct positioning of the device relative to a fracture without having to turn the device at an angle that will interfere with inserting a drill and/or fixing through the bore of the guide sleeve to an optimal site for fixing the fracture, and also without having to move the patient to an undesirable position to allow for access to the fracture.

Typically the guide device is adapted to close around a body portion, such as a fractured bone portion, and optionally to apply a clamping force to the body portion to clamp the body portion between the limbs as they pivot around their connection to close around the body portion.

Typically the orientation mechanism maintains the orientation of the guide sleeve relative to the body portion during pivotal movement of the limbs relative to one another.

Typically the bore of the guide sleeve is held in a defined orientation by the orientation mechanism, and optionally the axis of the bore of the guide sleeve intersects with the same point on the opposite limb of the device during pivotal movement of the limbs relative to one another.

The bore of the guide sleeve typically guides a drill bit and/or bone fixing device along the axis of the bore for insertion of the drill bit and/or fixing into the body portion along the axis.

Certain embodiments of the present invention allow the reduction of bone fractures (the clamping and fixing of two or more bone fragments together) at a particularly stable site for clamping, and can allow the insertion of a fixation system (i.e. drilling and inserting a pin or screw) into the same site (e.g. though the bore of the guide sleeve) for enhanced stability of the fixing. It is an advantage of such embodiments that when reducing the fracture, the bore of the guide sleeve typically points directly towards the opposite point of the device, and is typically held in alignment with the bore of the opposite guide sleeve regardless of what sized bone the surgeon is dealing with, and regardless of the spacing between the limbs. This can allow for the most stable clamping conditions, and can allow selection of the best side for drilling.

It will be appreciated that the benefits of a guide bore which is always oriented directly to the same position on the opposite limb of the device can be realised when only one of the first and second limbs has a guide sleeve attached thereto. This sleeve can be used to more accurately guide a drill bit and/or bone fixing (e.g. K-wire for temporary fixing or a screw for permanent fixing) into a desired position regardless of the relative angle between the limbs of the device. As compared to scissor-like devices, finer control is possible and a device according to the present invention can be particularly well suited to reducing small fractures e.g. in the delicate wrist or ankle bones.

In some embodiments, a single guide sleeve is provided on one of the limbs, and the other limb can optionally include a tissue engaging device.

In at least one preferred set of embodiments the device comprises first and second guide sleeves pivotally attached to the respective first and second limbs. Typically the device has a respective guide sleeve pivotally attached to each limb. In such embodiments the pivotal attachment of the guide sleeves ensures that the bore of the guide sleeve of each limb is always aligned with that of the other guide sleeve regardless of the angle between the limbs i.e. throughout the opening and closing of the device.

This feature may be considered novel and inventive in its own right, and thus according to a second aspect of the present invention there is provided a surgical guide device comprising first and second limbs pivotally connected together, a respective guide sleeve pivotally attached to each limb, each guide sleeve having a bore through the sleeve, and wherein the apparatus has an orientation mechanism adapted to change the orientation of the guide sleeves relative to the limbs as the limbs move relative to one another, so as to maintain the orientation of the guide sleeves relative to one another during pivotal movement of the limbs.

Typically the bore of each guide sleeve is held in a defined orientation by the orientation mechanism, and optionally the axis of the bore of one guide sleeve is always aligned with the axis of the bore of the other guide sleeve on the opposite limb of the device during pivotal movement of the limbs relative to one another. As is described above, the bore of each guide sleeve typically guides a drill bit and/or bone fixing device along the axis of the bore for insertion of the drill bit and/or fixing along the axis into a body portion clamped between the limbs.

It will be appreciated that a device in accordance with this second aspect of the invention and the embodiments described hereinabove may be particularly advantageous as it provides a surgeon with the increased flexibility of being able to insert a drill bit and/or bone fixing device through either or both of the guide devices attached to the two limbs (simultaneously or at different times). Such a device lends itself to a more symmetrical configuration that can make it easier for a surgeon to use the device single-handedly, with certainty of the orientation of the guide sleeves, whilst having a hand free.

In embodiments according to both aspects of the invention, the surgical guide device allows the clamping of bone fragments by movement of the guide sleeve(s) along a linear path, so that the guide sleeve(s) do not have an arcuate component to their travel before engaging a body portion, unlike scissor-type devices. Thus the trajectory of the guide sleeve(s) up to the stage where they engage the body portion, and the point on the body portion where they engage the body portion, can be more easily predicted and controlled.

There will now be described some features that generally apply whether the device comprises a single guide sleeve provided on one of the limbs or a respective guide sleeve pivotally attached to each limb. In the former case a dedicated tissue engaging device may be attached to the other limb while in the latter case at least one of the two guide sleeves may provide an engaging function, instead of or in addition to a guiding function. The tissue engaging device (and/or optionally the or each guide sleeve) can optionally be configured to retain a bone once the engaging device abuts it, and may optionally include a gripping formation adapted to resist sliding of the tissue engaging device off the surface of a bone, such as one or more spikes or tips or serrations which may pierce the surface of the bone. Alternatively or additionally, the tissue engaging device (and/or optionally the or each guide sleeve) can optionally incorporate an arcuate surface with a cup or curved plate or the like configured to conform to the shape of a bone surface in order to maintain the engagement between the bone and the tissue engaging device. In one embodiment of the invention, the or each or at least one guide sleeve and/or the tissue engaging device can have opposed inwardly facing arcuate surfaces with cups or curved plates that retain the arcuate outer surfaces of bones within their arc.

In one embodiment of the invention, the or each or at least one guide sleeve and/or the tissue engaging device can optionally incorporate swivel devices to allow at least the ends of the guide sleeves to rotate around their axes, so that the parts of the device that engage the tissue can rotate around their axes while supporting the body part. In such embodiments, the swivels can be free to move or can be restricted within limits of rotation, and can optionally adopt different and independent rotational positions with respect to one another.

Accordingly, the guide device on one limb applied to one side of the bone fragment can engage the bone and e.g. cup it securely in one rotational orientation, and the guide device on the other limb at the opposite side of the device can grip the same or a different bone in a different independent rotational position that suits the engagement between that guide sleeve and its bone portion, and is not necessarily dependent on the rotational position of the other guide sleeve.

The orientation mechanism typically maintains the orientation of each guide sleeve during pivotal movement of the limbs relative to one another.

Optionally each guide sleeve has a respective orientation mechanism.

Typically the bores of the guide sleeves are maintained in a mutually parallel orientation during pivotal movement of the limbs relative to one another.

Optionally the bores of the guide sleeves are maintained in an aligned orientation in which the axes of the bores of the guide sleeves coincide during pivotal movement of the limbs relative to one another.

A handle (such as a handle loop) can be provided on at least one limb, typically both, allowing operation of the device with a single hand.

The guide sleeve may be pivotally connected to a distal end of its limb at two points that are spaced apart on the guide sleeve.

Typically the limb comprises two limb portions that are movable relative to one another.

The orientation mechanism can maintain the two limb portions in the same orientation relative to one another e.g. parallel to one another during movement of the limbs relative to one another.

In some embodiments, the limb portions can be arranged telescopically. For example, in one embodiment, the limb portions can comprise at least one limb portion in the form of a tubular component with the other limb portion arranged within the bore of the tubular limb portion. In some cases, both limb portions can be tubular, arranged one within the other. In one such embodiment, the inner limb portion can move laterally with respect to the outer tube, within the bore of the outer tube, or axially.

In one embodiment with a tubular outer limb portion, the inner limb portion arranged inside the bore of the tubular limb portion can optionally be in the form of a stiff wire or cable that is axially inextensible and incompressible, but typically has at least a portion that is laterally flexible. Typically the laterally flexible portion of the wire or cable of the inner limb is encased in a housing, which may optionally comprise the bore of the tubular outer limb, so that the axial transmission of movement of the inner limb within the casing is accurately translated from the top of the limb to the guide sleeve, typically resulting in movement of the guide sleeve to maintain the parallel relationship between the guide sleeve and the yoke during movement of the limb. The bore of the tubular limb portion can be circular or non-circular, which can be useful to resist rotation of the inner limb portion within the outer while allowing axial translation.

Encasing one limb portion within the other reduces the exposure of moving parts to the patient and operator, and reduces risk of erroneously catching body portions between the limb portions.

Optionally the two limb portions are pivotally coupled to the guide sleeve at the distal end of the limb, and typically to a yoke device at the proximal end of the limb.

The pivot points between the limb portions, the guide sleeve and the yoke device can optionally together form an expanding and collapsing parallelogram. The pivot points can be defined at the corners of the parallelogram. The limbs can optionally form the sides of the parallelogram, but in some cases the sides can be straight or can incorporate arcuate portions to curve around body parts being supported. The limb portions defining the parallelogram can optionally remain parallel while allowing lateral movement of the opposite limbs relative to one another.

Typically the orientation mechanism maintains the guide sleeve parallel to the yoke when the limbs move relative to one another.

In some embodiments, the orientation mechanism can comprise a toothed mechanism having two or more toothed members that mesh together to control the movement of the limbs and/or the movement of the guide sleeves relative to the limbs. Typically the toothed members can be gears, but toothed rails and other forms of toothed member can be used. Typically the toothed members coordinate the separation between the limbs, optionally ensuring that movement of one limb results in equal movement of the other limb at the same speed, and typically in the opposite direction, thereby coordinating the movement of the limbs. The toothed members can also act between the limbs and the guide sleeve in some embodiments, controlling (and optionally synchronising) the pivotal movement of the guide sleeve(s) relative to its limb.

In some embodiments, the toothed members can comprise disc gears mounted on the limbs, optionally at the pivot points connecting the limbs to the yoke. The gears typically mesh together to transfer force between the limbs, so that as one limb moves relative to the yoke, the other limb is driven through the meshed gears by the same amount, in the opposite rotational direction. Therefore, the toothed members on the orientation mechanism keep the limbs at mirrored angles relative to the yoke as the limbs separate. Since the angles between the limb and the yoke are kept as mirrors of one another, the separation of the limbs from the central position between the limbs is the same, so the guide sleeves at the ends of the limbs are therefore also spaced from the central position by the same amount. As the guide sleeves and the limbs are spaced apart by the same distance from the central position, so the orientation bars connecting the guide sleeves to the yoke are also moved by equal amounts, thereby maintaining the orientation of the guide sleeves during the coordinated movement of the limbs.

The orientation mechanism typically comprises a gear arranged to mesh with one of the limb portions.

Optionally, the orientation mechanism is provided at a connection between the limbs.

Alternatively, or in addition, the orientation mechanism is optionally provided at the or each guide sleeve.

Optionally the orientation mechanism can comprise a linkage incorporating a constraint mechanism such as a pin movable within a slot which controls (e.g. restricts) movement of the limbs relative to one another (and typically relative to the yoke) so that different relative positions of the pin and the slot correspond to different positions of the limbs with different lateral separations. Instead of the pin and slot the orientation mechanism can optionally comprise a bar movable within a bore. The constraint mechanism can optionally be connected to the limbs or the handles by means of pivotally connected bars. The pivotally connected bars are typically connected to the limbs above the yoke, and are pivotally connected to a pivot point on a constraining bar. The pivot point is typically slidable in a linear manner with respect to the yoke as the limbs separate. The sliding of the pivot point can be constrained by the slot or by the bar movable within the bore. The bore can be provided through the yoke or through the pivot point.

An orientation mechanism comprising an expanding and collapsing parallelogram or a linkage mechanism may be preferred to a toothed mechanism as the former mechanisms may be more robust in operation and better able to withstand the potentially large clamping forces involved in reducing a major bone fracture. A geared mechanism, on the other hand, may be more susceptible to wear with the teeth of the gears possibly slipping under the application of larger forces. A parallelogram or linkage mechanism may also be simpler to manufacture with the required tolerances.

Optionally the bore of the guide sleeve is adapted to receive and optionally retain a bone engaging device, such as a wire (e.g. a Kirschner wire or "K-wire" or an olive wire), a drill, a screw, a nail or such like. In one embodiment, the bore of the guide sleeve can comprise or can optionally be adapted to receive and optionally retain a cannulated insert, typically with a sharp pointed tip, adapted to anchor the guide sleeve against movement in relation to a body portion such as a bone.

Optionally, the bore of the guide sleeve is adapted to receive a drill device, such as a drill bit.

Certain embodiments permit the identification or prediction of the path of a drill bit through the guide sleeve, thereby reducing the risk of drilling through sensitive or critical tissues, and increasing the chances of anchoring the fixing in solid tissues that are more capable of withstanding forces tending to dislodge the fixing after insertion.

In some embodiments, the or each or at least one guide sleeve can have a cylindrical bore. In some embodiments the bore can be non-circular, e.g. square or oval or irregular with one or more flats, which can be of assistance in maintaining the rotational orientation of a fixing device or cannulated insert within the bore.

In some embodiments, a positive stop or shoulder can be provided on the limbs or the yoke, to limit the maximum and minimum separation of the limbs during operation of the device.

The invention according to a further aspect also provides a method of guiding the insertion of a fixing device into a body portion, comprising providing a guide device comprising first and second limbs pivotally connected together to close around the body portion, having at least one guide sleeve attached to one limb, the guide sleeve having a bore through the sleeve, wherein the guide sleeve is pivotally attached to the limb, and wherein the apparatus has an orientation mechanism adapted to change the orientation of the guide sleeve relative to the limb as the limbs move relative to one another, the method comprising closing the limbs of the clamp device around the body portion until the guide sleeve engages the body portion, and controlling the orientation of the guide sleeve relative to the body by means of the orientation mechanism, and inserting a fixing device into the body portion through the bore in the guide sleeve.

The fixing device can be a screw or pin etc. that remains in place in the body, or can be a drill or pin wire that is withdrawn from the body portion after it forms a hole or guides the path of insertion of a separate fixing device.

Inserts adapted to be received within the bores of the guide sleeves are typically inserted into the sleeves from the outer ends of the sleeves. In some embodiments, inserts can be inserted through the inner facing ends of the sleeves.

There will now be described some further features that are optionally applicable to all the aspects of the invention outlined above.

In some embodiments with more than one guide sleeve, the guide sleeves can be symmetrical, e.g. tubular in cross section. The guide sleeves may optionally receive and optionally retain (e.g. by means of screw threads or other attachment mechanisms) sleeves of smaller dimensions adapted to fit within the guide sleeves, and may be used to provide a smaller bore of guide sleeve for a K-wire or drill.

In some embodiments, the limbs can have a locking device adapted to either limit the maximum separation of the limbs relative to one another, and/or to lock the separation at fixed distance between the guide sleeves. A ratchet mechanism can be provided between the limbs to lock the limbs against lateral movement in one direction. A measurement device can optionally be provided between the limbs to indicate to a user the distance between the limbs, for example the distance between the guide sleeves at their opposing tips. The measurement device may, for example, be integrally provided by the locking device.

Optionally the guide sleeves can be aligned on the same axis, and can be maintained in that orientation throughout the range of movement of the limbs, but in some embodiments, the guide sleeves can be maintained in some different orientation, for example, with intersecting axes.

In certain embodiments the guide sleeves can be applied to bone faces at normal angles.

The guide sleeves can optionally incorporate locking mechanisms to lock components within the sleeves. Locking mechanisms may include threads (optionally of different hands) bayonet fittings, etc. In one embodiment, the guide sleeves can optionally be at least partially threaded, and the bores can typically receive threaded inserts to cooperate with the threads on the guide sleeves, so that the threaded inserts can be locked in position within the bore of the sleeve, withstanding axial forces tending to back the inserts out of the bore during clamping, and also allowing the inserts to be axially advanced or retracted within the sleeve by virtue of the threads to apply or reduce force to the body after the limbs have been closed around the body.

In some embodiments of the invention a force mechanism can be provided between the limbs such as a threaded rod and a collar, to apply force between the limbs to open and close them by means of the force mechanism.

In one embodiment, the two limbs can be releasably connected together e.g. at the yoke. The releasable connection can option comprise a head on one of the limbs and a slot on the other. The head can optionally fit through the slot in one configuration, e.g. in one rotational configuration, allowing the two limbs to be separated and connected in that configuration, and can optionally resist disconnection between the limbs in other configurations, typically different rotational configurations of the limbs relative to one another. For example, the head can comprise a T-shaped head connected to one limb by a cylindrical bar, and adapted to fit snugly through a slot on the other limb, when the head is offered to the slot in a particular rotational configuration in which the head is aligned with the slot, for example, when the two limbs are splayed and the guide sleeves are far apart. When the head passes through the slot the limbs are connected together and can be closed to rotate the head out of alignment with the slot and thereby resist separation of the two limbs. The device can then be used as previously described. When the limbs are to be separated e.g. after the procedure, they are splayed to bring the head into alignment with the slot so that the head can pass back through the slot and the two limbs can separate. This modification allows the two limbs to be assembled and disassembled separately around the part of the body to be manipulated. The yoke can optionally have a slot to accept the head. The two limbs could also be secured together by means of a hand operated fastening such as a wing nut. The fastening could optionally pass through the fulcrum for the pivotal movement of the limbs, but embodiments could be constructed in which the fastening passed through other parts of the yoke, and the fulcrum and any associated gears were already set in place and required no assembly, adjustment or meshing before use. Optionally the slot could allow the fulcrum to slide axially along the slot within the confines of the slot.

According to a preferred set of embodiments, the limbs, or at least one of the limbs, is optionally at least partially curved to accommodate one or more body portions between them. This may make it easier for the guide sleeve(s) to be suitably manipulated into place around a body portion e.g. bone fragment to be pinned within a body. The curved portion(s) of the limb(s) may also provide an X-ray beam path to reach the fracture site without interference, thereby enabling the fracture to be imaged during the reduction and fixing process. The curved portion(s) of the limb(s) can optionally lie in the same plane as the limb(s), or in more than one plane.

In one set of embodiments at least one of the limbs, preferably both the first and second limbs, of the device is curved or bent in the plane (e.g. x-y plane) of the limb(s). Optionally this is the main plane of the device as a whole, although in some embodiments there may be other parts of the device, such as finger loops, that extend out of the main x-y plane. Where the guide sleeve meets the other limb, or where the two guide sleeves meet, there can be defined an orthogonal plane (e.g. z plane) relative to the axis of the guide sleeve(s). Preferably the or each limb is curved or bent in the x-y plane of the limbs so as to increase the spacing of the limb(s) from this z-plane. Such a curve or bend in the limb(s) helps to prevent pinching of tissue between the bone portion held between the limbs and the rest of the device. It can also improve the line of vision for the surgeon and also for x-ray beams which are used to confirm that a fixing is in the correct position and that the bone has been aligned as required. The curved or bent portions of the limb(s) can therefore prevent the device from restricting the line of vision.

In one set of embodiments at least one of the limbs, preferably both the first and second limbs, of the device is curved or bent in a plane (e.g. z plane) that is out of the plane (e.g. x-y plane) of the limb(s). Such a z-plane may be at angle θ (0<θ<90° to the x-y plane or substantially orthogonal to the x-y plane. As is described above, such a curve or bend in the limb(s) can prevent the device from restricting the line of vision.

In one set of embodiments at least one of the limbs, preferably both the first and second limbs, of the device is curved or bent both in the plane (e.g. x-y plane) of the limb(s) and out of the plane (e.g. x-y plane) of the limb(s). By providing the limb(s) with a bend in two planes the line of vision may be optimised so that the device does not interfere with viewing and/or imaging a body portion clamped between the limbs.

The various embodiments of the present invention can be practiced alone or in combination with one or more of the other embodiments, as will be appreciated by those skilled in the relevant arts. The various aspects of the invention can optionally be provided in combination with one or more of the optional features of the other aspects of the invention. Also, optional features described in relation to one embodiment can typically be combined alone or together with other features in different embodiments of the invention.

Various embodiments and aspects of the invention will now be described in detail, by way of example only, with reference to the accompanying figures. Still other aspects, features, and advantages of the present invention are readily apparent from the entire description thereof, including the figures, which illustrates a number of exemplary embodiments and aspects and implementations. However, the drawings and descriptions are to be regarded as illustrative in nature, and not as restrictive.

BRIEF DESCRIPTION OF THE DRAWINGS

In the accompanying drawings:

FIG. 1 is a front view of a first embodiment of a surgical guide device shown in a closed configuration;

FIG. 2 is a front view of the FIG. 1 device shown in an open configuration;

FIG. 3 is a front view of a second embodiment of a surgical guide device;

FIG. 4 is a perspective view of the FIG. 3 device;

FIG. 5 is an exploded view of the FIG. 4 device;

FIG. 6 is a close up perspective view of a part of the FIG. 3 embodiment;

FIG. 8 is a front view of a third embodiment of a surgical guide device;

FIG. 9 is a view from one side of the FIG. 8 embodiment;

FIG. 10 is a view from the other side of the FIG. 8 embodiment;

DETAILED DESCRIPTION OF THE INVENTION

Figure 7:
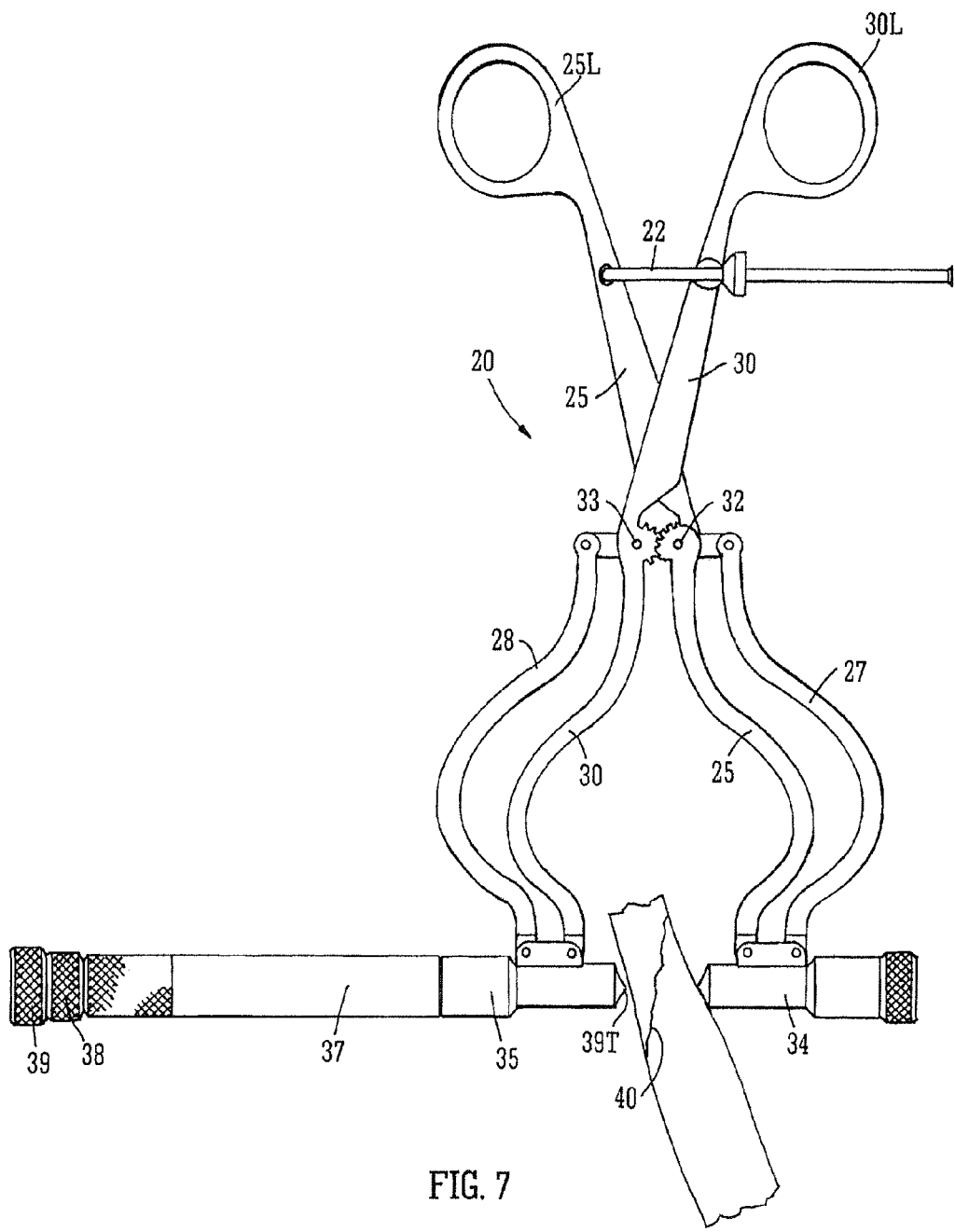
FIG. 7 is a front view of the FIG. 3 embodiment closed around a fracture.

Referring now to the drawings, FIGS. 1 and 2 show closed and open configurations of a first embodiment of a surgical guide device 1 having a pair of limbs 5, 10, having handle loops 5L, 10L at a proximal end and bone-engaging devices at the distal ends. In the first embodiment of the device 1, the limbs comprise a reference limb 5 and a moveable limb 10. At the distal end of the reference limb 5, the bone-engaging device takes the form of a stud 12 which has a pointed tip adapted to securely engage against the outer surface of a piece of bone to be clamped using the device 1. At the distal end of the moveable limb 10, the bone-engaging device comprises a guide sleeve 14, having a central bore to receive a drill or the like, and to allow the drill to pass through the guide sleeve 14. The guide sleeve 14 has a flange 14*f* extending radially with respect to the bore from an outer surface of the guide sleeve 14. The guide sleeve is typically tubular, and can optionally have a partially pointed tip to engage the surface of a bone fragment to be fixed, for example by pinning. The flange 14*f* typically provides an anchor point for pivotally connecting the distal end of the moveable limb 10 to the flange 14*f* of the guide sleeve 14. The connection is typically in the form of a rivet or the like, allowing pivotal movement of the guide sleeve 14 around the pivot point at the distal end of the moveable leg 10.

The reference limb 5 typically has a yoke 6 extending latterly from a mid-point of the reference limb 5. The yoke 6 typically provides an anchor point for connecting an orientation control bar 7 between the yoke 6 and the guide sleeve 14. The pivot point connecting the orientation bar 7 at its upper end to the yoke 6 is typically spaced laterally from the pivot point connecting the two limbs 5, 10. The bar 7 is typically attached to the guide sleeve 14 at its distal end, at a pivot point similarly spaced (typically by the same distance) from the pivot point between the guide sleeve 14 and the movable limb. Thus the orientation bar 7 forms part of a connection between the limbs 5, 10, and is pivotally connected between them. The orientation bar 7 typically restrains the range of movement of the guide sleeve 14, so that the guide sleeve 14 is maintained in an advantageous orientation throughout its range of movement, as shown by contrasting the open and closed configurations of FIGS. 1 and 2. In each case, the orientation bar 7, the movable limb 10, the yoke 6 and the guide sleeve 14 are all pivotally interconnected and form a collapsing and expanding parallelogram arrangement, which maintains the orientation of opposite sides relative to one another. Thus when the movable limb 10 is moved relative to the reference limb 5, the guide sleeve 14 moves, but is kept in the same orientation by the action of the collapsing parallelogram arrangement. Therefore, when the guide sleeve meets the outer surface of a piece of bone, and is used to clamp two bone fragments together while a hole is drilled or a guide wire (e.g. a K-wire) is inserted through the bore in the guide sleeve, the operator knows that the orientation of the bore (and therefore the path of the hole to be drilled or K-wire to be inserted) is always substantially parallel to the axis of the yoke 6, and will not vary (within limits) even while the movable leg 10 moves pivotally in an arc relative to the reference leg 5 and the yoke 6. Therefore, the path of the bore to be drilled through the guide sleeve 14 can be estimated with greater accuracy, avoiding sensitive tissues, and can be aimed with greater accuracy through dense bone in the most advantageous position for the retention of the fixing in the bone fragments.

Also, the operator can clamp the bone fragments together in the best position on the bone to clamp the fragments together, and can also drill through the same site, without releasing the clamping force.

A second embodiment of a guide device 20 is shown in FIGS. 3-7. The second embodiment of the device 20 has two limbs 25, 30 that are pivotally connected to a central yoke 26, and each limb 25, 30 is pivotally movable relative to the yoke 26. Each limb has a loop 25L, 30L at its proximal end and a respective guide sleeve 34, 35 at its distal end. The guide sleeves 34, 35 have a pair of parallel flanges 34F, 35F defining between them a groove to receive the distal ends of the limbs, and which are bored to received pivot pins such as rivets or bolts to pivotally connect the guide sleeves to the limbs. The guide sleeves 34, 35 have axial bores to receive inserts 37, 38 and 39, which can optionally be cannulated and can have sequentially decreasing sizes of axial bore to provide different sizes of bores along the same axis in the event that the device 20 is to be used with different diameters of drills. The inserts typically screw into threads in the necks of the bores in the guide sleeves, to resist axial forces applied to them when urged against the bone surface during clamping operations.

The bores in the guide sleeves 34, 35 can optionally receive (and typically retain by means of the screw threads) clamping pins 36 which are not cannulated, and which can optionally terminate in a point or a cup 36T, or some other formation adapted to resist lateral slippage of the pin 36 across the outer surface of a bone fragment when clamping force is applied to the device. Typically the final insert 39 in the guide sleeve 35 can be a solid pin extending the length of the bore of the guide sleeve 35 and the previous inserts, and terminating in a sharp tip 39T to resist lateral slippage off the bone when clamped against a fractured bone (see FIG. 7).

The second embodiment of the device 20 has a respective orientation control bar 27, 28 for each limb 25, 30. As can best be seen in FIG. 6, the control bars 27, 28 are connected to the limbs 25, 30 by means of the yoke 26. The yoke 26 is pivotally connected to each of the limbs 25, 30, and to each of the control bars 27, 28 through pivot pins such as rivets or bolts or such like. The heads of the bars 27, 28, and optionally the limbs 25, 30 can be slotted to receive and retain the yoke 26 within the slot.

Optionally, the relative movement of the limbs 25, 30 and the yoke 26 around the pivot points is controlled by intermeshing toothed members in this embodiment in the form of disc gears 32, 33, mounted respectively on limbs 25 and 30. In this embodiment, the gears 32, 33 are of similar diameter, and can be mounted on bolts extending through the pivot points between the limbs 25, 30 and the yoke 26, so that relative pivotal movement of one of the limbs (e.g. 25) initiates and controls the movement of the other limb 30 to the same extent, but typically in the opposite direction. Typically each of the limbs 25, 30 moves in opposite directions by the same amount and at the same speed, although the direction and speed or range can optionally be changed by modifying the direction of rotation of the gears (e.g. by introducing an intermediate gear) or changing the meshing diameter of one or both of the gears 32, 33. Linear toothed members such as bars can also be used in some embodiments.

As with the previous embodiment, the pivots between the bars 27, 28 and the limbs 25, 30 are spaced apart and together define the corners of a collapsing and expanding parallelogram, which keeps the guide sleeves 34, 35 in the same orientation (generally parallel to the yoke 26 and aligned with one another) during movement of the limbs 25, 30 around the pivot points.

In this embodiment, the gears 32, 33 coordinate the separation of the limbs 25, 30, while the orientation bars 27, 28 coordinate the pivotal movement of the guide sleeves 34, relative to the limbs 25, 30. The gears 32, 33 mesh together to transfer force between the limbs 25, 30, so that as the operator opens the handle loops 25L, 30L, both limbs 25, 30 move relative to the yoke 26 in opposite rotational directions and at the same speed, keeping the limbs 25, 30 at mirrored angles relative to the yoke 26 as the limbs 25, 30 separate. The yoke 26 effectively remains static relative to the oppositely moving limbs 25, 30. Since the angles between the limbs 25, 30 and the yoke 26 are kept as mirrors of one another, the separation of the limbs 25, 30 from the central axis X between the limbs 25, 30 is the same, so the guide sleeves 34, 35 at the ends of the limbs 25, 30 are therefore also spaced from the central axis X by the same amount. As the guide sleeves 34, 35 and the limbs 25, 30 are spaced apart by the same distance from the central axis X, so the orientation bars 27, 28 connecting the guide sleeves 34, 35 to the yoke 26 are also moved by equal amounts, thereby maintaining the orientation of the guide sleeves 34, 35 parallel to the yoke 26 during the coordinated movement of the limbs 25, 30.

The extent of separation of the limbs 25, 30 is typically controlled (e.g. limited) and maintained by means of a screw clamp device 22, or by a ratchet face device (not shown). In the present embodiment, the limbs 25, 30 can optionally be at least partially curved to accommodate body portions between them, and allow the guide sleeves 34, 35 to be suitably manipulated into place on opposite sides of a bone fragment to be pinned within a body. The curved portions of the limbs 25, 30 can optionally lie in the same plane, or in more than one plane. The curved portions of the limbs 25, 30 may also provide an X-ray beam path to reach the fracture site without interference, thereby enabling the fracture to be imaged during the reduction and fixing process.

In the present embodiment of a device 20, because of the action of the orientation control bars, the bores of each of the guide sleeves 34, 35 are substantially always in alignment with one another despite changes in separation between the limbs 25, 30 as a result of arcuate movement of the limbs 25, 30 around the pivot points, and despite changes in orientations of the limbs 25, 30 and their respective orientation bars 27, 28. Therefore, it can be seen that since the guide sleeve bores substantially always face one another, the line of insertion of a drill or K-wire or other bone fixing device, and its point of emergence on the opposite side (i.e. within the opposite guide sleeve) can be more reliably predicted even when gripping bones of very different sizes. As with the previous embodiment, the clamp device 20 allows clamping and drilling through the same (e.g. the most stable) point of the clamped fracture. Furthermore, the operator can be sure that penetration of the drill through the opposite wall of the bone will result in emergence of the drill into the opposite guide sleeve, isolated from tissues, and therefore allows accurate bone drilling with reduced chances of damaging tissues by emergence of the drill bit from the other side of the bone at unpredictable locations.

One other advantageous aspect of this embodiment is that an operator can clamp in the best location, secure the clamp in place using the locking bar 22, and then choose between the two sides of the clamped bone for drilling, depending on free space on each side for drilling equipment, and without consideration of damaging the tissues by emergence of the drill through the bone in unpredictable locations.

In use, the device 20 according to the second embodiment can be used as shown in FIG. 3, with a respective pin 36 in each of the guide sleeves 34, 35. However, in some cases, the inserts can be used when the device is placed around a fracture 40. In such cases, the device 20 is assembled as shown in FIG. 7 with all of the inserts 37, 38, 39 screwed into the guide bore 35 and a pin 36 within the guide bore 34. The device 20 is then opened and placed around the fracture 40 to be clamped (not shown to scale). The handles of the limbs are pressed together to close the guide sleeves 34, 35 around the fracture 40. The locking device 22 is then typically applied to lock the limbs 25, 30 at the desired angle. The limbs 25, 30 pivot around the yoke 26 until the bone fragments to be clamped are pressed tightly together at the fracture 40 between the guide sleeves 34, 35. When the desired clamping force has been applied, the limbs 25, 30 are typically locked in position by means of the locking bar 22, and the pin 39 is removed from the guide sleeve 35, to allow access by a K-wire or drill bit through the narrow bore of the insert 38. If a larger diameter of drill bit or K-wire is to be used (instead of the K-wire or subsequent to it)

then the second insert 38 is removed and the drill bit is inserted through the larger bore in insert 37. If the bore in insert 37 is also too narrow, then it can be removed and the drill can be operated through the bore of the sleeve 35. Optionally the location of the guide sleeves 34, 35 can be adjusted, e.g. pressed harder against the bone by pressing the handles together during or after the removal of the inserts, or even during drilling to keep compression on the fracture, or increase it or reduce it, while maintaining the position of the clamping force at the most stable point on the bone during drilling operations along the same axis.

The orientation of the guide sleeves 34, 35 is maintained by the orientation bars 27, 28, and so they remain in the same orientation during the movement of the limbs 25, 30, and when the guide sleeves 34, 35 engage the outer surface of the bone to be drilled, the operator can be confident that the axis of the bores in each of the guide sleeves 34, 35 is parallel to the yoke 26 and that the bores are aligned with one another.

Once the hole has been drilled, or the K-wire inserted, the device 20 can be removed from the patient, allowing accurate insertion of bone fixing devices. However, it is especially advantageous to leave the device 20 in place and deploy the screws or other bone fixings through the channels provided by the guide sleeves 34, 35, to fix the bone fragments together while the clamping force is maintained.

After drilling or inserting a K-wire, with the device 20 still clamped in place, the separation distance of the limbs 25, 30 can advantageously be used to directly measure the width of the bone fragments either side of the fracture 40 and hence to determine the length of screw or other bone fixing required. For example, the screw clamp 22 or other lock bar extending between the limbs 25, 30 may be provided with gradations or indicia to indicate the separation distance of the tips that are clamped against the bone fragments. The indicia may be scaled depending on the relative distances of the clamp bar 22 and the guide sleeves 34, 35 from the pivot points. This advantageous feature may be applied to any of the further embodiments described hereinbelow.

An exemplary method of guiding the insertion of a fixing device into a bone fracture site using a guide device 20 according to the second embodiment is set out in Table 1.

TABLE 1

| Step | Action | Procedure |
|---|---|---|
| 1 | Gain access to fracture | Utilise standard surgical procedures to gain preferred access to bone and fracture site |
| 2 | Locate forceps in fracture region | Place the forceps device 20 with 2 x short spikes 36 on bone at desired reduction/fixation sites and compress with hand |
| 3 | Reduce fracture with 2 x short spikes | Use combination of grip strength and leverage through tightening the locking nut on the locking bar 22 until fracture is reduced to desired level. |
| 4 | Visualise reduction and potential fixation placement | Visualise directly or indirectly (using fluoroscopic images) the placement of the forceps device 20, reduction of fracture and chosen line of screw placement to ensure that the correct set-up has been achieved. If not, repeat steps 1-4 until this has been achieved. |
| 5 | Remove 1 x short spike | Whilst gently holding the forceps device 20 in place with one hand, unscrew and remove one of the short spikes 36 from the preferred side of forceps through which fracture fixation is to take place (working side). The guide sleeves 34, 35 have teeth to grip the bone and retain the position of the guide sleeve. However, depending upon the shape of the bone, it may be necessary to compress the tips of the forceps and to re-tighten the locking nut to compensate for any tendency for the fracture gap to open or for the forceps to displace. Note - Upon removal of the short spike 36 an approximate 1.5 mm gap will occur between bone and forceps on the working side. |
| 6 | Screw in drill sleeve set | Whilst still holding forceps device 20 in position by hand, screw in the drill sleeve set to the guide sleeve 34, 35 on the working side. Note - Once the drill sleeve set has been fully screwed in, the distal end of the guide-wire sleeve will compress the fracture to the exact same extent as the previous set-up with the initial short spike. As with stage 5 above, some adjustment may need to be made to optimise fracture position and forceps tip pressure. |
| 7 | Fix fracture with guide-wire | Use standard surgical techniques and drill to insert a guide-wire through the guide-wire sleeve to temporarily stabilise the fracture. |
| 8 | Measure length of screw required | Assuming that the surgeon is happy that the length of the guide-wire inserted is an accurate representation of the final screw length to be inserted, it is possible to choose the correct screw length by reading the length marked guide-wire against the outermost portion of the guide-wire sleeve. |
| 9 | Remove medium insert sleeve | Remove the medium insert by unscrewing it from drill sleeve set whilst holding knurled top of large insert. Slightly tighten the locking nut on bar 22 to re-apply compression caused by removing the guide-wire sleeve and 'tighten' forceps onto the bone. |
| 10 | Drill bone | Using a dedicated cannulated drill placed over the guide-wire, drill the bone to the desired depth (usually extending from one tip of the forceps to the other tip). |
| 11 | Measure length of screw required | An alternative method for assessing the desired screw length is possible by reading the length marked drill bit against the outer most portion of the drill sleeve. Alternatively both the drill bit and guide wire can be removed and using a standard depth gauge, define the length of the drill hole and length of screw required to be inserted through the working end. |
| 12 | Remove large insert sleeve | Remove large insert by unscrewing it from drill sleeve set whilst holding forceps and guide sleeve and applying gentle compression to maintain fracture reduction and correct positioning of the forceps. |
| 13 | Tighten locking screw wheel | If required slightly tighten locking nut to re-apply compression caused by removing large insert and 'tighten' forceps on bone. **NB - This step may be obsolete, since the points on the cannulated channels may grip the bone enough, so that the removal of the large insert has no effect on the stability of the forceps. |
| 14 | Insert screw/cannulated screw | For cannulated screw insertion, the guide-wire would remain in place after the drill hole has been created. |

TABLE 1-continued

| Step | Action | Procedure |
|---|---|---|
| | | Thereafter, the screw would be inserted with a standard cannulated screw driver. Alternatively, where the surgeon has elected to use a normal screw, this will be inserted in a standard fashion after removing the guide-wire. |
| 15 | Visualisation of screw placement and fixation | Direct visualisation of the fracture reduction and correct positioning of the screw will be possible in some instances. However, in many cases, indirect methods of visualising the fracture and screw position will be achieved using fluoroscopy. |
| 16 | Remove forceps | Loosen locking nut, disengage locking bar 22 and remove forceps from patient. |
| 17 | Close wounds | Close surgical wounds utilising standard surgical procedures. |

A third embodiment is shown in FIGS. 8-13. This third embodiment of a guide device 50 is similar to the second embodiment 20 in terms of structure and operation, and has two limbs 55, 60 that are pivotally connected to a central yoke 56 in the same way as the second embodiment, each limb having a respective orientation control bar 57, 58 that is curved in two planes (contrast FIG. 8 with FIGS. 9 & 10). Each limb has a loop 55L, 60L at its proximal end and a respective guide sleeve 64, 65 at its distal end. The guide sleeves 64, 65 have flanges defining a groove to pivotally connect to the distal ends of the limbs 55, 60. The guide sleeves 64, 65 have axial bores to receive inserts 67, 68 and 69, which can optionally be cannulated and optionally threaded (at least partially) and can have sequentially decreasing sizes of axial bore to provide different sizes of bores along the same axis in the event that the device 50 is to be used with different diameters of drills, K-wires or other fixings. The inserts 67, 68, 69 can be screwed into the guide sleeves 64, 65 as before, to resist axial forces applied to them. The bores in the guide sleeves 64, 65 can optionally receive (and typically retain by means of the screw threads) clamping pins which are not cannulated, and which can optionally terminate in a point or a cup, or some other formation adapted to resist lateral slippage of the guide sleeve 64, 65 across the outer surface of a bone fragment when clamping force is applied to the device. The cup also assists in spreading loads between the device and the bone. Cups also assist in centralising the guide sleeve on the bone.

In the third embodiment, the guide sleeves 64, 65 are typically non-identical, one of them 64 being shorter than the other 65. The shorter guide sleeve 64 can be used to access smaller spaces within the body to allow the clamp 50 to be placed appropriately around a fracture to be clamped. The smaller guide sleeve 64 can optionally accommodate a pin (not shown, but similar to pin 36) to retain the shorter sleeve on a bone surface during clamping. The longer guide sleeve 65 can be used to accommodate different sizes of insert with different diameters of bore, so that the drill can be properly supported within the bore of the guide sleeve 65 during drilling. Note that only one guide sleeve 65 is necessary in the present embodiment, and the guide sleeve 64, containing the pin, can optionally be changed for a solid pin without a sleeve, which can typically be adapted to pivot to remain in the same orientation during closing of the limbs.

In use, the guide device 50 according to the third embodiment is typically assembled with all of the inserts 67, 68, 69 screwed into the bore of the guide sleeve 65 and a pin within the bore of the guide sleeve 64. The device 50 is then opened to the configuration shown in FIG. 10, typically to an extent sufficient to permit it to be placed around the fracture to be clamped. The handles of the limbs are pressed together to close the guide sleeves 64, 65 around the fracture.

As in the previous embodiment, the gears 62, 63 coordinate the separation of the limbs 55, 60, while the orientation bars 58, 58 coordinate the pivotal movement of the guide sleeves 64, 65 relative to the limbs 55, 60. The gears 62, 63 mesh together to transfer force between the limbs 55, 60, so that as the operator opens the handle loops 55L, 60L, both limbs move relative to the yoke 56 in opposite rotational directions and at the same speed, keeping the limbs at mirrored angles relative to the yoke 56 as the limbs 55, 60 separate. The yoke 56 effectively is held static relative to the oppositely moving limbs 55, 60 and remains in the same starting orientation. Since the angles between the limbs 55, 60 and the yoke 56 are kept as mirrors of one another, the separation of the limbs 55, 60 from the central axis X between the limbs 55, 60 is the same, so the guide sleeves 64, 65 at the ends of the limbs 55, 60 are therefore also spaced from the central axis X by the same amount. As the guide sleeves 64, 65 and the limbs 55, 60 are spaced apart by the same distance from the central axis X, so the orientation bars 57, 58 connecting the guide sleeves 64, 65 to the yoke 56 are also moved by equal amounts, thereby maintaining the orientation of the guide sleeves 64, 65 parallel to the yoke 56 during the coordinated movement of the limbs 55, 60.

Figure 11:
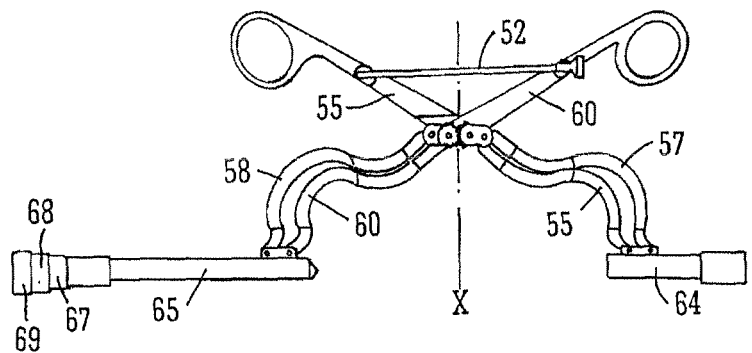
FIGS. 11, 12 and 13 are front views showing sequential configurations of the FIG. 8 embodiment from the open configuration shown in FIG. 11 to the closed configuration shown in FIG. 13.
Figure 12:
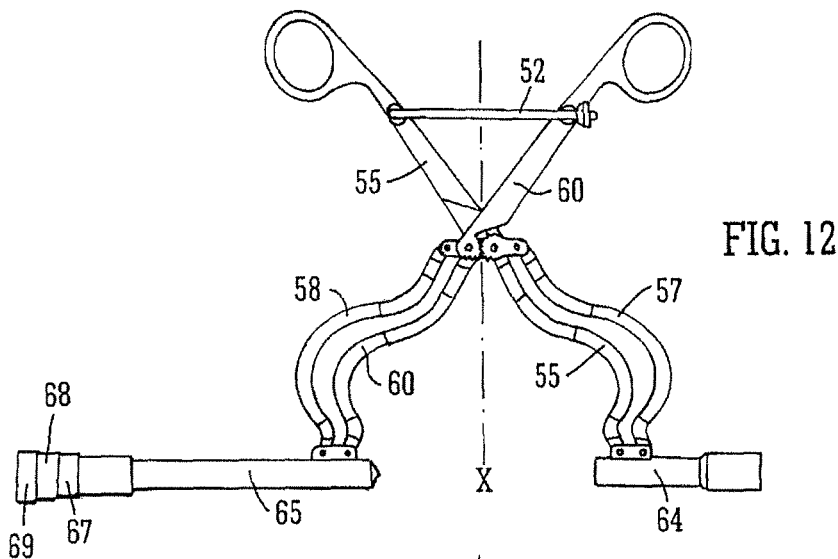
Figure 13:
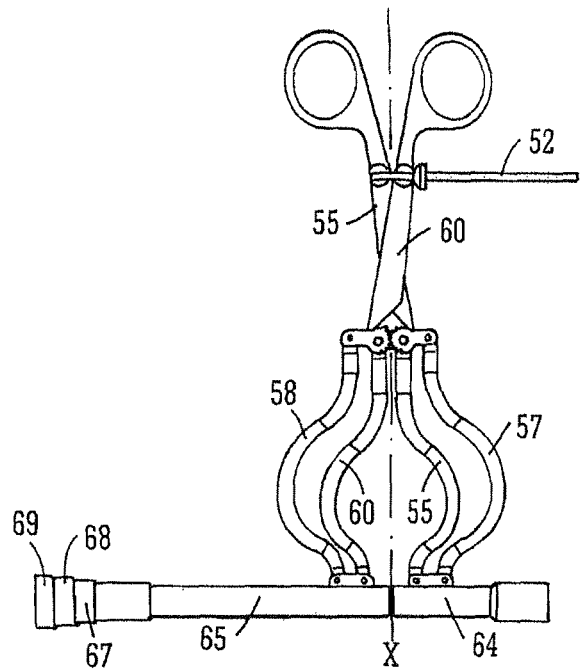

The limbs 55, 60 are moved pivotally around the yoke 56 between the different configurations shown in FIGS. 10-12, until the bone fragments to be clamped are pressed tightly together between the guide sleeves 64, 65. When the desired clamping force has been applied, the limbs 55, 60 are locked in position by tightening the locking nut of the locking bar 52 against the anchor point on the limb 60. At that point, the pin 69 is removed from the longer guide sleeve 65, to allow access by a K-wire or drill bit through the narrow bore of the insert 68. If a larger diameter of drill bit or K-wire is to be used, then the second insert 68 is removed and the drill bit is inserted through the larger bore in insert 67. If the bore in insert 67 is also too narrow, then it can be removed and the drill can be operated through the bore of the sleeve 65. Optionally the guide sleeves 64, 65 can be adjusted e.g. tightened up by pressing the handles together and/or tightening the nut on the locking bar during or after the removal of the inserts, or even during drilling to keep a constant compression on the fracture, at the most stable point on the bone.

The separation between the limbs 55, 60 is coordinated by the gears 62, 63. The orientation of the guide sleeves 64, 65 during separation is maintained by the orientation bars 57, 58, and so they remain in the same orientation during the movement of the limbs 55, 60, and when the guide sleeves 64, 65 engage the outer surface of the bone to be drilled, the operator can be confident that the axis of the bores in each of the guide sleeves 64, 65 is parallel to the yoke 56 and that the bores are aligned with one another.

Once the hole has been drilled, or the K-wire inserted, the device 50 can be removed from the patient, allowing accurate insertion of bone fixing devices. Alternatively the device can be left in place and the screws or other bone fixings can be deployed through the channels provided by the guide sleeves, to fix the bone fragments together while the clamping force is maintained.

Figure 14:
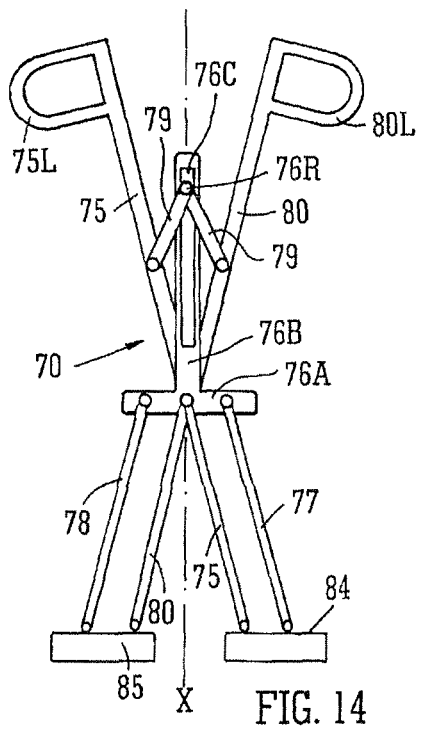
FIG. 14 is a front view of a fourth embodiment of a surgical guide device.

A fourth embodiment is shown in FIG. 14. This fourth embodiment of a guide device 70 has two straight limbs 75, 80 that are pivotally connected to a central yoke 76 in the same way as the second embodiment, each limb having a respective orientation control bar 77, 78, a loop 75L, 80L at its proximal end and a respective guide sleeve 84, 85 at its distal end. The limbs, loops etc and the guide sleeves 84, 85 are shown schematically here but are essentially the same as in earlier embodiments, e.g. the second or third embodiment.

The device 70 of the fourth embodiment has a different form of yoke 76. The yoke 76 has an inverted T shape, with a main bar 76A being retained parallel to the guide sleeves 84 by means of the orientation mechanism, a bar extension 76B slotted at 76C with a linear slot to receive a rivet 76R connecting link arms 79, which are pivotally connected together at the rivet 76R intersecting the slot 76C. The arms 79 are also pivotally connected to the limbs 75 and 80 between the loops 75L, 80L and the yoke 76.

In use, the device 70 according to the fourth embodiment is opened to the configuration shown in FIG. 14 typically to an extent sufficient to permit it to be placed around the fracture to be clamped. The handles of the limbs 75, 80 are pressed together to close the guide sleeves 84, 85 around the fracture.

Instead of using gears to coordinate the separation of the limbs 75, 80, the device 70 of the fourth embodiment uses the link arms 79, while the orientation bars 78, 77 coordinate the pivotal movement of the guide sleeves 84, 85 relative to the limbs 75, 80. Such a linkage mechanism may be preferred to a gearing mechanism as it can be more robust in operation and withstand the potentially large clamping forces involved in reducing a major bone fracture. A geared mechanism, on the other hand, may be more susceptible to wear with the teeth of the gear wheels possibly slipping under the application of larger forces. A linkage mechanism may also be simpler to manufacture with the required tolerances.

The link arms 79 move together around the pivot points so that as the operator opens the handle loops 75L, 80L, the rivet 76r slides in the slot 76c and both limbs 75, 80 move relative to the yoke 76 in opposite rotational directions and at the same speed, keeping the limbs 75, 80 at mirrored angles relative to the yoke 76 as the limbs 75, 80 separate. The yoke 76 effectively is held static relative to the oppositely moving limbs 75, 80 and remains in the same starting orientation. Since the angles between the limbs 75, 80 and the yoke 76 are kept as mirrors of one another, the separation of the limbs 75, 80 from the central axis X between the limbs 75, 80 is the same, so the guide sleeves 84, 85 at the ends of the limbs 75, 80 are therefore also spaced from the central axis by the same amount. As the guide sleeves 84, 85 and the limbs 75, 80 are spaced apart by the same distance from the central axis X, so the orientation bars 77, 78 connecting the guide sleeves 84, 85 to the yoke 76 are also moved by equal amounts, thereby maintaining the orientation of the guide sleeves 84, 85 parallel to the yoke 76 during the coordinated movement of the limbs 75, 80.

The limbs 75, 80 are moved pivotally around the yoke 76 until the bone fragments to be connected are pressed together between the guide sleeves 84, 85. When the desired clamping force has been applied, the limbs 75, 80 are locked in position and the fixing device is inserted as previously described.

The separation between the limbs 75, 80 is coordinated by the link arms 79. The orientation of the guide sleeves 84, 85 during separation is maintained by the orientation bars 77, 78, and so they remain in the same orientation during the movement of the limbs 75, 80, and when the guide sleeves 84, 85 engage the outer surface of the bone to be drilled, the operator can be confident that the axis of the bores in each of the guide sleeves 84, 85 is parallel to the yoke 76 and that the bores are aligned with one another.

Figure 15:
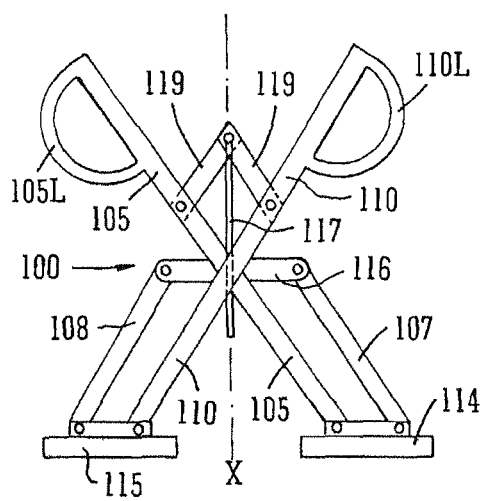
FIGS. 15 and 16 are open and closed configurations of a fifth embodiment of a surgical guide device.
Figure 16:
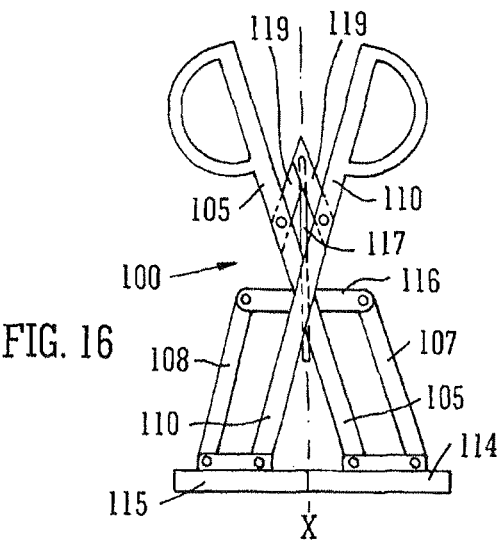

A fifth embodiment is shown in FIGS. 15 and 16. In this embodiment the device 100 has two straight limbs 105, 110 that are pivotally connected to a central yoke 116 in the same way as the previous embodiment, each limb 105, 110 having a respective orientation control bar 107, 108, a loop 105L, 110L at its proximal end and a respective guide sleeve 114, 115 at its distal end. The limbs, loops etc and the guide sleeves are shown schematically here but are essentially the same as in earlier embodiments, e.g. the second or third embodiment.

The fifth embodiment has a different form of yoke 116. The yoke 116 is a plain bar held parallel to the guide sleeves 114, 115 by means of the orientation mechanism, having a central bore passing through the bar and being perpendicular to the bar, for receiving a cylindrical rod 117 that slides through the bore along the axis of closure of the device 100 and which is pivotally connected at its upper end to link arms 119, which are pivotally connected together at their connection to the rod 117. The arms 119 are also pivotally connected to the limbs 105 and 110 between the loops and the yoke 116.

In use, the device 100 of the fifth embodiment is opened to the configuration shown in FIG. 15 typically to an extent sufficient to permit it to be placed around the fracture to be clamped. The handles of the limbs 105, 110 are pressed together to close the guide sleeves 114, 115 around the fracture.

Like the previous embodiment, in the fifth embodiment the device 100 uses the link arms 119 to control the separation of the limbs 105, 110, while the orientation bars 107, 108 coordinate the pivotal movement of the guide sleeves 114, 115 relative to the limbs 105, 110. Such a linkage mechanism may be more robust than a geared mechanism, as is discussed above.

The link arms 119 move together around the pivot points so that as the operator opens the handle loops 105L, 110L, the rod 117 slides in the aperture through the yoke 116 and both limbs 105, 110 move relative to the yoke 116 in opposite rotational directions and at the same speed, keeping the limbs 105, 110 at mirrored angles relative to the yoke 116 as the limbs 105, 110 separate. The yoke 116 effectively is held static relative to the oppositely moving limbs 105, 110 and remains in the same starting orientation. Since the angles between the limbs 105, 110 and the yoke 116 are kept as mirrors of one another, the separation of the limbs 105, 110 from the central axis X between the limbs 105, 110 is the same, so the guide sleeves 114, 115 at the ends of the limbs 105, 110 are therefore also spaced from the central axis by the same amount. As the guide sleeves 114, 115 and the limbs 105, 110 are spaced apart by the same distance from the central axis X, so the orientation bars 107, 108 connecting the guide sleeves 114, 115 to the yoke 116 are also moved by equal amounts, thereby maintaining the orientation of the guide sleeves 114, 115 parallel to the yoke 116 during the coordinated movement of the limbs 105, 110.

The limbs 105, 110 are moved pivotally around the yoke 116 until the bone fragments to be connected are pressed together between the guide sleeves 114, 115. When the desired clamping force has been applied, the limbs 105, 110 are locked in position and the fixing device is inserted as previously described.

The separation between the limbs 105, 110 is coordinated by the link arms 119. The orientation of the guide sleeves 114, 115 during separation is maintained by the orientation bars 117, 118, and so they remain in the same orientation during the movement of the limbs 105, 110, and when the guide sleeves 114, 115 engage the outer surface of the bone to be drilled, the operator can be confident that the axis of the bores in each of the guide sleeves 114, 115 is parallel to the yoke 116 and that the bores are aligned with one another.

Figure 17:
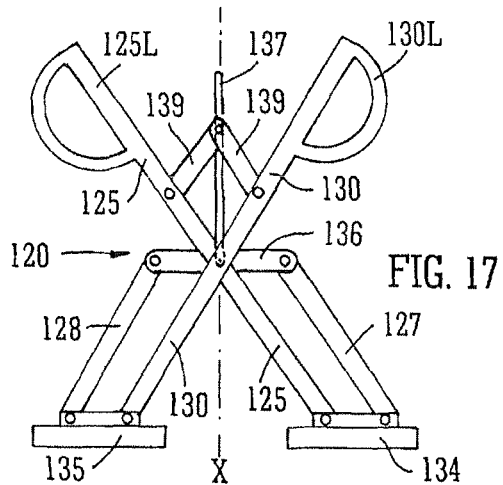
FIGS. 17 and 18 are open and closed configurations of a sixth embodiment of a surgical guide device.
Figure 18:
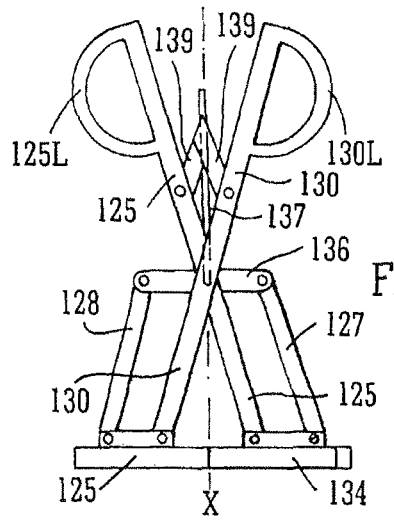

A sixth embodiment is shown in FIGS. 17 and 18. In this embodiment the device 120 is essentially the same as the device 100 of the previous embodiment, but has a different form of yoke 136. The yoke 136 is a plain bar held parallel to the guide sleeves 134, 135 by means of the orientation mechanism. The yoke 136 has a cylindrical rod 137 that is rigidly connected to the yoke 136 and extends perpendicular to it, along the axis of closure of the device. The rod 137 passes through an apertured pivot connector at its upper end, which allows the rod to slide through the connector, in the same way as the rod 117 can slide through the aperture in the yoke 136 of the earlier embodiment. The connector connects the rod to link arms 139, which are pivotally connected together at their connection to the rod 137. The arms 139 are also pivotally connected to the limbs 125, 130 between the loops 125L, 130L and the yoke 136.

In use, a device 120 according to the sixth embodiment is opened and placed around the fracture. The handles of the limbs 125, 130 are pressed together to close the guide sleeves 134, 135 around the fracture.

Like the previous embodiment, the device 120 of the sixth embodiment uses the link arms 139 to control the separation of the limbs 125, 130, while the orientation bars 127, 128 coordinate the pivotal movement of the guide sleeves 134, 135 relative to the limbs. Again, such a linkage mechanism may be preferred to a geared mechanism at least for the reasons outline above.

The link arms 139 move together around the pivot points so that as the operator opens the handle loops the rod 137 slides in the apertured connector and both limbs 125, 130 move relative to the yoke 136 in opposite rotational directions and at the same speed, keeping the limbs 125, 130 at mirrored angles relative to the yoke 136 as the limbs 125, 130 separate. The yoke 136 effectively is held static relative to the oppositely moving limbs 125, 130 and remains in the same starting orientation. Since the angles between the limbs 125, 130 and the yoke 136 are kept as mirrors of one another, the separation of the limbs from the central axis X between the limbs 125, 130 is the same, so the guide sleeves 134, 135 at the ends of the limbs 125, 130 are therefore also spaced from the central axis by the same amount. As the guide sleeves 134, 135 and the limbs 125, 130 are spaced apart by the same distance from the central axis X, so the orientation bars 127, 128 connecting the guide sleeves 134, 135 to the yoke 136 are also moved by equal amounts, thereby maintaining the orientation of the guide sleeves 134, 135 parallel to the yoke 136 during the coordinated movement of the limbs.

The limbs are moved pivotally around the yoke 136 until the bone fragments to be connected are pressed together between the guide sleeves 134, 135. When the desired clamping force has been applied, the limbs are locked in position and the fixing device is inserted as previously described.

The separation between the limbs 125, 130 is coordinated by the link arms 139. The orientation of the guide sleeves 134, 135 during separation is maintained by the orientation bars 127, 128, and so they remain in the same orientation during the movement of the limbs 125, 130, and when the guide sleeves 134, 135 engage the outer surface of the bone to be drilled, the operator can be confident that the axis of the bores in each of the guide sleeves 134, 135 is parallel to the yoke 136 and that the bores are aligned with one another.

The rods 117 and 137 can be cylindrical and can have a circular cross section and slide in a circular hole, or alternatively the rods can have a non-circular cross section and can be retained in a hole of matching shape, and so can remain rotationally static.

Figure 19:
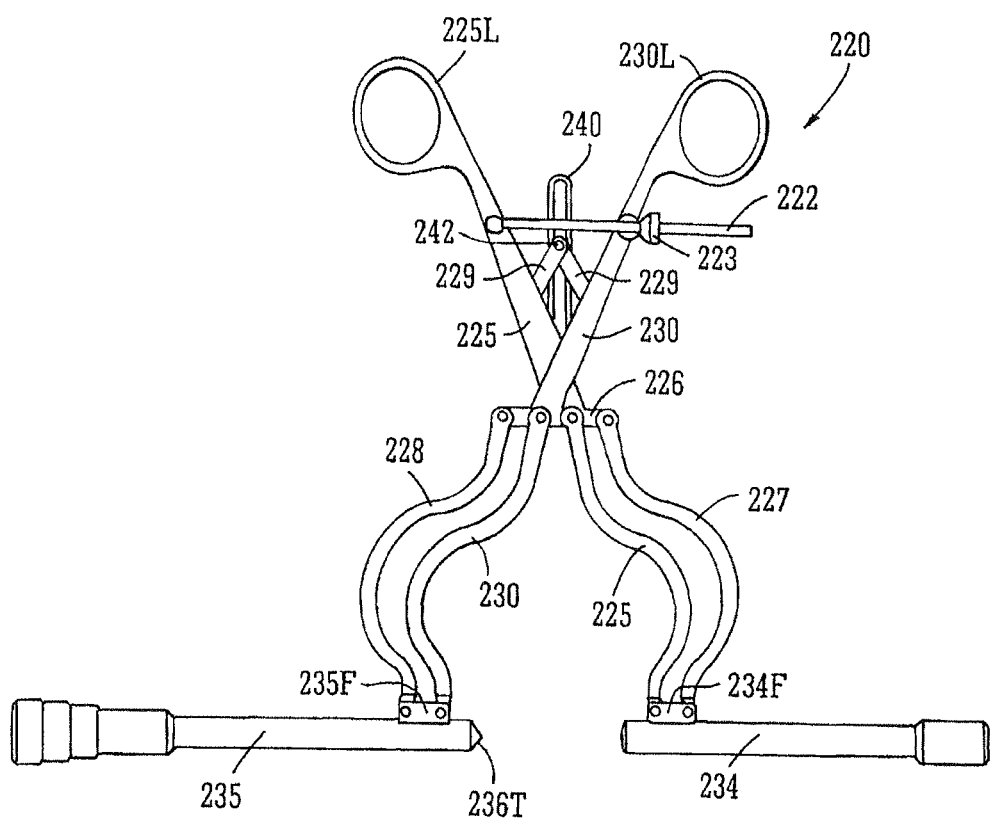
FIG. 19 is a front view of a seventh embodiment of a surgical guide device.

A seventh embodiment is shown in FIG. 19. In this embodiment the device 220 is a hybrid that takes the design of the limbs from the second and third embodiments shown in FIGS. 3 to 13, but instead of a geared mechanism there is provided a linkage mechanism having the same design as the fourth embodiment of FIG. 14. Without going into detail, it can be seen that the device 220 has two limbs 225, 230 that are pivotally connected to a central yoke 226, and each limb 225, 230 is pivotally movable relative to the yoke 226. Each limb has a finger loop 225L, 230L at its proximal end and a respective guide sleeve 234, 235 at its distal end. The guide sleeves 234, 235 have a pair of parallel flanges 234F, 235F defining between them a groove to receive the distal ends of the limbs, and which are bored to received pivot pins such as rivets or bolts to pivotally connect the guide sleeves to the limbs. The guide sleeves 234, 235 have axial bores to receive inserts, which can optionally be cannulated and can have sequentially decreasing sizes of axial bore to provide different sizes of bores along the same axis in the event that the device 220 is to be used with different diameters of drills.

The bores in the guide sleeves 234, 235 can optionally receive (and typically retain by means of screw threads) clamping pins 236 which are not cannulated, and which can optionally terminate in a point or a cup 236T, or some other formation adapted to resist lateral slippage of the pin 236 across the outer surface of a bone fragment when clamping force is applied to the device.

The device 220 has a respective orientation control bar 227, 228 for each limb 225, 230. The control bars 227, 228 are connected to the limbs 225, 230 by means of the yoke 226. The yoke 226 is pivotally connected to each of the limbs 225, 230, and to each of the control bars 227, 228 through pivot pins such as rivets or bolts or such like. Although not shown, the heads of the bars 227, 228, and optionally the limbs 225, 230 can be slotted to receive and retain the yoke 226 within the slot. Because of the action of the orientation control bars 227, 228, the bores of each of the guide sleeves 234, 235 are substantially always in alignment with one another despite changes in separation between the limbs 225, 230 as a result of arcuate movement of the limbs 225, 230 around the pivot points, and despite changes in orientations of the limbs 225, 230 and their respective orientation bars 227, 228.

The extent of separation of the limbs 225, 230 is typically controlled (e.g. limited) and maintained by means of a screw clamp device comprising a locking bar 222 and a locking nut 223, or by a ratchet device (not shown). A surgeon can clamp a bone portion in the best location, secure the clamp in place using the locking bar 222 and nut 223, and then choose between the two sides of the clamped bone for drilling, depending on free space on each side for drilling equipment.

The limbs 225, 230 can optionally be at least partially curved to accommodate body portions between them, and to allow the guide sleeves 234, 235 to be suitably manipulated into place on opposite sides of a bone fragment to be pinned within a body. The curved portions of the limbs 225, 230 can optionally lie in the same plane, or in more than one plane.

Instead of using gears to coordinate the separation of the limbs 225, 230, the device 220 uses a linkage mechanism comprising a pair of link arms 229. The yoke 226 includes an orthogonally extending slotted bar 240 that receives a rivet 242 connecting the two link arms 229, which are pivotally connected together at the rivet 242 intersecting the slot. The arms 229 are also pivotally connected to the limbs 225 and 230 between the loops 225L, 230L and the yoke 226.

The link arms 229 move together around the pivot points so that as the operator opens the handle loops 225L, 230L, the rivet 242 slides in the slot of the bar 240 and both limbs 225, 230 move relative to the yoke 226 in opposite rotational directions and at the same speed, keeping the limbs 225, 230 at mirrored angles relative to the yoke 226 as the limbs 225, 230 separate. The yoke 226 effectively is held static relative to the oppositely moving limbs 225, 230 and remains in the same starting orientation. Since the angles between the limbs 225, 230 and the yoke 226 are kept as mirrors of one another, the separation of the limbs 225, 230 from the central axis between the limbs 225, 230 is the same, so the guide sleeves 234, 235 at the ends of the limbs 225, 230 are therefore also spaced from the central axis by the same amount. As the guide sleeves 234, 235 and the limbs 225, 230 are spaced apart by the same distance from the central axis, so the orientation bars 227, 228 connecting the guide sleeves 234, 235 to the yoke 226 are also moved by equal amounts, thereby maintaining the orientation of the guide sleeves 234, 235 parallel to the yoke 226 during the coordinated movement of the limbs 225, 230.

The limbs 225, 230 are moved pivotally around the yoke 226 until the bone fragments to be connected are pressed together between the guide sleeves 234, 235. When the desired clamping force has been applied, the limbs 225, 230 are locked in position and a fixing device is inserted as previously described. Since the guide sleeves 234, 235 remain in the same orientation during movement of the limbs 225, 230, a surgeon can be confident that the axis of the bores in each of the guide sleeves 234, 235 is parallel to the yoke 226 and that the bores are aligned with one another.

Although the present invention has been described with reference to preferred embodiments, it will be understood by those skilled in the art that various changes in form and detail may be made, and modifications and improvements can be incorporated, without departing from the scope of the invention as set forth in the accompanying claims.

The invention claimed is:

1. A surgical guide device comprising first and second limbs pivotally connected together, at least one guide sleeve attached to one limb, the guide sleeve having a bore through the sleeve, wherein the guide sleeve is pivotally attached to the limb, and wherein the apparatus has an orientation mechanism adapted to change the orientation of the guide sleeve relative to the limb as the limbs move relative to one another;
    wherein the bore of the at least one guide sleeve is held in a defined orientation by the orientation mechanism, and the axis of the bore of the guide sleeve intersects with the same point on the opposite limb of the device during pivotal movements of the limbs relative to one another;
    wherein the first limb comprises two limb portions that are moveable relative to one another; and
    wherein the two limb portions are pivotally coupled to the guide sleeve at the distal end of the first limb and to a yoke device at the proximal end of the first limb.

2. A surgical guide device as claimed in claim 1, wherein the guide device is adapted to close around a body portion, and optionally to apply a clamping force to the body portion to clamp the body portion between the limbs as they pivot around their connection to close around the body portion.

3. A surgical guide device as claimed in claim 1, wherein the orientation mechanism maintains the orientation of the guide sleeve relative to the body portion during pivotal movement of the limbs relative to one another.

4. A surgical guide device as claimed in claim 1, wherein a single guide sleeve is provided on one of the limbs, and the other limb can optionally include a tissue engaging device.

5. A surgical guide device as claimed in claim 4, wherein the tissue engaging device or the guide sleeve is configured to retain a bone and includes a gripping formation adapted to resist sliding off or along the surface of a bone.

6. A surgical guide device as claimed in claim 1, wherein the device has a respective guide sleeve pivotally attached to each of the first and second limbs.

7. A surgical guide device as claimed in claim 1, wherein the at least one guide sleeve is adapted receive and optionally retain sleeves of smaller dimensions adapted to fit within the guide sleeves.

8. A surgical guide device as claimed in claim 1, wherein the at least one guide sleeve incorporates a locking mechanism to lock one or more component(s) within the sleeve(s).

9. A surgical guide device as claimed in claim 1, wherein the at least one guide sleeve is pivotally connected to a distal end of the one limb at two points that are spaced apart on the guide sleeve.

10. A surgical guide device as claimed in claim 1, wherein a handle is provided on at least one limb, optionally on both limbs, allowing operation of the device with a single hand.

11. A surgical guide device as claimed in claim 1, wherein the first and second limbs have a locking device adapted to limit the maximum separation of the limbs relative to one another, or to lock the separation at a fixed distance.

12. A surgical guide device as claimed in claim 1, wherein a force mechanism is provided between the first and second limbs to apply force between the limbs to open and close them.

13. A surgical guide device as claimed in claim 1, wherein at least one of the first and second limbs is at least partially curved to accommodate one or more body portions between them.

14. A surgical guide device as claimed in claim 13, wherein at least one of the first and second limbs comprises a curved portion that lies in the same plane as the limb(s).

15. A surgical guide device comprising first and second limbs pivotally connected together, a respective guide sleeve pivotally attached to each limb, each guide sleeve having a bore through the sleeve, and wherein the apparatus has an orientation mechanism adapted to change the orientation of the guide sleeves relative to the limbs as the limbs move relative to one another, so as to maintain the orientation of the guide sleeves relative to one another during pivotal movement of the limbs;
    wherein the bore of each guide sleeve is held in a defined orientation by the orientation mechanism such that the axis of the bore of one guide sleeve is always aligned with the axis of the bore of the other guide sleeve on the opposite limb of the device during pivotal movement of the limbs relative to one another;
    wherein the first limb comprises two limb portions that are moveable relative to one another; and
    wherein the two limb portions are pivotally coupled to the guide sleeve at the distal end of the first limb and to a yoke device at the proximal end of the first limb.

16. A method of guiding the insertion of a fixing device into a body portion, comprising providing a guide device comprising first and second limbs pivotally connected together to close around the body portion, having at least one guide sleeve attached to one limb, the guide sleeve having a bore through the sleeve, wherein the guide sleeve is pivotally attached to the limb, and wherein the apparatus has an orientation mechanism adapted to change the orientation of the guide sleeve relative to the limb as the limbs move relative to one another,
    wherein the bore of the at least one guide sleeve is held in a defined orientation by the orientation mechanism, and the axis of the bore of the guide sleeve intersects with the same point on the opposite limb of the device during pivotal movements of the limbs relative to one another;

wherein the first limb comprises two limb portions that are moveable relative to one another; and wherein the two limb portions are pivotally coupled to the guide sleeve at the distal end of the first limb and to a yoke device at the proximal end of the first limb;

the method comprising closing the limbs of the clamp device around the body portion until the guide sleeve engages the body portion, and controlling the orientation of the guide sleeve relative to the body by means of the orientation mechanism, and inserting a fixing device into the body portion through the bore in the guide sleeve.

17. A surgical guide device comprising:

first and second limbs pivotally connected together, a guide sleeve attached to the first limb, the guide sleeve having a bore through the sleeve, wherein the guide sleeve is pivotally attached to the first limb, and wherein the guide device has an orientation mechanism adapted to change the orientation of the guide sleeve relative to the first limb as the limbs move relative to one another;

wherein the bore of the guide sleeve is held in a defined orientation by the orientation mechanism, and the axis of the bore of the guide sleeve intersects with the same point on the opposite limb of the device during pivotal movement of the limbs relative to one another;

wherein the first limb comprises two limb portions that are movable relative to one another; and said guide device further comprising a yoke device;

wherein the two limb portions are pivotally coupled to the guide sleeve at the distal end of the first limb, at two points that are spaced apart on the guide sleeve; and wherein pivot points between the two limb portions, the guide sleeve and the yoke device together form an expanding and collapsing parallelogram.

18. A surgical guide device as claimed in claim 17, wherein the second limb comprises a tissue engaging device.

19. A surgical guide device as claimed in claim 17, further comprising a second guide sleeve or a solid pin, wherein the second guide sleeve or solid pin is pivotally attached to the second limb.

20. A surgical guide device as claimed in claim 19 wherein the bore of the guide sleeve on the first limb is always aligned with the bore of the second guide sleeve on the second limb or remains in the same orientation as the solid pin on the second limb.

21. A surgical guide device as claimed in claim 19 wherein the separation of the first and second limbs from a central axis between the first and second limbs is equal to the separation of the first guide sleeve and the second guide sleeve or solid pin from the central axis.

22. A surgical guide device as claimed in claim 17, wherein the second limb comprises two limb portions, that are movable relative to one another, wherein the two limb portions are pivotally coupled to the second guide sleeve or solid pin at the distal end of the second limb, at two points that are spaced apart on second guide sleeve or solid pin; and wherein pivot points between the two limb portions, the second guide sleeve or solid pin and the yoke device together form a second expanding and collapsing parallelogram.

23. A surgical guide as claimed in claim 17, wherein the or each guide sleeve is configured to retain a bone and includes a gripping formation adapted to resist sliding off or along the surface of a bone.

24. A surgical guide device as claimed in claim 17, wherein the orientation mechanism comprises a toothed mechanism having two or more toothed members that mesh together to control the movement of the limbs.

25. A surgical guide device as claimed in claim 17, wherein the orientation mechanism comprises a linkage incorporating a constraint mechanism which controls movement of the limbs relative to one another.

26. A surgical guide device as claimed in claim 25, wherein the constraint mechanism comprises a pin or bar movable within a slot or bore which controls movement of the limbs relative to one another so that different relative positions of the pin or bar and the slot or bore correspond to different positions of the limbs with different lateral separations.

27. A surgical guide device as claimed in claim 17, wherein the or each guide sleeve is adapted to receive and optionally retain sleeves of smaller dimensions adapted to fit within the guide sleeves.

28. A surgical guide device as claimed in claim 17, wherein the or each guide sleeve incorporates a locking mechanism to lock one or more component(s) within the sleeve(s).

29. A surgical guide device as claimed in claim 17 wherein the bore of the or each guide sleeve is at least partially threaded so that a threaded insert received in the bore can be locked in position within the bore of the sleeve.

30. A surgical guide device as claimed in claim 17, wherein the limbs have a locking device adapted to limit the maximum separation of the limbs relative to one another.

31. A surgical guide device as claimed in claim 17, wherein at least one of the first and second limbs is at least partially curved to accommodate one or more body portions between them.

32. A surgical guide device as claimed in claim 17, wherein at least one of the first and second limbs comprises a curved portion that lies in the same plane as the limb(s) and/or lies in more than one plane.

33. A surgical guide device as claimed in claim 17, wherein the first and second limbs are configured to rotate in opposite directions, at the same speed and at mirror angles relative to the yoke.

34. A surgical guide device as claimed in claim 17, wherein the orientation mechanism maintains the guide sleeve parallel to the yoke.

35. A surgical guide device as claimed in claim 17 wherein the pivot points are defined at the corners of the parallelogram and the limb portions incorporate arcuate portions to curve around body parts being supported.

36. A method of guiding the insertion of a fixing device into a body portion with a guide device including first and second limbs pivotally connected together to close around the body portion, having at least one guide sleeve attached to one limb, the guide sleeve having a bore through the sleeve, wherein the guide sleeve is pivotally attached to the limb, wherein the guide device has an orientation mechanism adapted to change the orientation of the guide sleeve relative to the limb as the limbs move relative to one another, wherein the bore of the guide sleeve is held in a defined orientation by the orientation mechanism, and the axis of the bore of the guide sleeve intersects with the same point on the opposite limb of the device during pivotal movement of the limbs relative to one another, and wherein the first limb comprises two limb portions that are movable relative to one another, said guide device further including a yoke device, wherein the two limb portions are pivotally coupled to the guide sleeve at the distal end of the first limb, at two points that are spaced apart on the guide sleeve, and wherein pivot points between the two limb portions, the guide sleeve and the yoke device together form an expanding and collapsing parallelogram, the method comprising:

closing the limbs of the clamp device around the body portion until the guide sleeve engages the body portion;

controlling the orientation of the guide sleeve relative to the body by means of the orientation mechanism; and inserting a fixing device into the body portion through the bore in the guide sleeve.

* * * * *